United States Patent [19]

Muir et al.

[11] 4,061,732

[45] Dec. 6, 1977

[54] CONTROL OF LACTIC ACIDOSIS IN RUMINANTS

[75] Inventors: Larry A. Muir, Flemington; Albert Barreto, Milltown, both of N.J.

[73] Assignee: Merck & Co., Inc., Rahway, N.J.

[21] Appl. No.: 739,929

[22] Filed: Nov. 8, 1976

Related U.S. Application Data

[63] Continuation-in-part of Ser. No. 668,332, March 19, 1976, abandoned, which is a continuation of Ser. No. 527,392, Nov. 26, 1974, abandoned, which is a continuation of Ser. No. 444,991, Feb. 22, 1974, abandoned.

[51] Int. Cl.$^2$ ............................................. A61K 35/00
[52] U.S. Cl. ..................................................... 424/117
[58] Field of Search ......................................... 424/117

[56] References Cited

U.S. PATENT DOCUMENTS

| | | | |
|---|---|---|---|
| 3,761,587 | 9/1973 | Miyairi | 424/117 |
| 3,790,668 | 2/1974 | Raun | 424/117 |

*Primary Examiner*—Sam Rosen
*Attorney, Agent, or Firm*—David L. Rose; J. Jerome Behan

[57] ABSTRACT

The nutritional disease, lactic acidosis, is successfully prevented by orally administering to the animal an effective amount of a sulfur-containing peptide antibiotic. In particular thiopeptin and thiostrepton are particularly effective sulfur-containing peptide antibiotics useful against lactic acidosis.

12 Claims, No Drawings

CONTROL OF LACTIC ACIDOSIS IN RUMINANTS

RELATIONSHIP TO OTHER APPLICATIONS

This application is a continuation-in-part of our co-pending application Ser. No. 668,332 filed Mar. 19, 1976, now abandoned, which in turn is a continuation of Ser. No. 527,392 filed Nov. 26, 1974, now abandoned, which in turn is a continuation of Ser. No. 444,991 filed Feb. 22, 1974, now abandoned.

BACKGROUND OF THE INVENTION

Lactic acidosis has long been recognized as a nutritional disease that often occurs in ruminants following an extra large intake of readily fermentable carbohydrate. Traditionally, lactic acidosis occurred when cattle accidently gained access to the farmer's grain fields or grain supply. Today with the advent of high concentrate rations for cattle, lactic acidosis occurs frequently in high producing dairy cows that are placed on high concentrate diets too quickly following initiation of lactation; in feedlot cattle that are rushed too quickly onto high concentrate rations and more subtly in feedlot cattle that are adapted to high concentrate consumption but experience changes in ration or feeding pattern.

In particular, lactic acidosis is a serious problem in cattle during the first few weeks in the feedlot because of the stress due to starvation from shipping and conversion from a roughage to a concentrate diet. Cattle normally consume 10-12 meals per day which allows rumen microbes to thrive. When no feed is ingested for a prolonged period, such as when cattle are shipped to the feedlot, most protozoa and many types of rumen bacteria perish. The lactate producer *Streptococcus bovis*, however, survives starvation better than most rumen microbes so that starvation increases the relative number of *Streptococcus bovis*. Most bacteria in the rumen are gram negative and are involved in the conversion of dietary carbohydrates to volatile fatty acids. *Streptococcus bovis* on the other hand is a gram positive rumen microorganism that converts readily fermentable carbohydrates to DL-lactic acid. Normally *Streptococcus bovis* does not play a predominant role in rumen fermentation and lactic acid is a minor product of rumen fermentation, however, when ruminants not adapted to high starch ration consume large quantities of readily fermentable carbohydrate *Streptococcus bovis* multiplies rapidly often outgrowing all other rumen microorganisms, and produces great quantities of DL-lactic acid. The lactic acid lowers rumen fluid pH which prevents normal fermentation by inhibiting other rumen microorganisms and eventually enables lactobacillus, another lactic acid producer, to establish itself in the rumen. The large quantities of DL-lactic acid produced in the rumen are absorbed. L-lactic acid is metabolized by the animal but D-lactic acid accumulates in the blood causing a depletion of the alkali reserve and a shift in blood pH which can cause death.

Lactic acidosis is a major problem in feedlot cattle. Lactic acidosis causes a significant loss in animal production even when the animal survives because of conditions associated directly or indirectly with the disease. These conditions include anorexia, rumen disfunction, diarrhea, weight loss, founder and rumenitis. Rumenitis, an ulceration of the ruminal wall, allows rumen microorganisms especially *Spherophorus necrophorus* to gain access to the portal circulatory system. These microbes are removed by the liver where they cause liver abscesses which reduce weight gain and feed efficiency. In addition, the abscessed livers are condemned at slaughter resulting in further economic losses. Thus lactic acidosis reduces animal productivity not only through death losses but also through reduced performance caused by poor animal health. The only known method of preventing lactic acidosis is to slowly adapt cattle to a high energy ration. The time required to adapt cattle is not well defined, however, most cattle feeders allow at least 3 to 4 weeks. During this time most feeders gradually switch from a ration having a concentrate to roughage ratio of 1:3 to a ration having a ratio of 3:1 or higher. One of the problems with this approach is that the low energy rations used initially do not produce sufficient energy for restoration of animal health and disease resistance following the stress of shipping to the feedlot. In addition, slow adaptation does not allow for rapid adjustment to fattening (high energy) rations which cost the cattle feeder time and money. None of the antibiotics presently available for use in ruminants control lactic acidosis.

It is an aspect of this invention that the antibiotics employed in the treatment of lactic acidosis be effective against the microorganism *Streptococcus bovis*, however, all antibiotics effective against *Streptococcus bovis* may not be effective against lactic acidosis. Should the antibiotic destroy significant numbers of rumen microorganisms beyond *Streptococcus bovis* then rumen functions will effectively cease and metabolism of ingested feed will also cease resulting in serious nutritive disorders. Normal rumen bacteria consists primarily of gram negative bacteria. Thus it is also an aspect of this invention that the antibiotic have a spectrum substantially limited to gram positive bacteria and excluding the majority of the normal rumen bacteria in order that the normal rumen microorganisms not be effected so that normal rumen function continues while the antibiotic is being administered to the ruminant.

DESCRIPTION OF THE INVENTION

Thus it is an object of the instant invention to provide for a method for the prevention of lactic acidosis in ruminants. Another object is to provide for the oral administration of an agent to prevent the occurrence of lactic acidosis in ruminants. A further object is to provide for a method for the prophylactic or therapeutic treatment of lactic acidosis in ruminants employing sulfur-containing peptide antibiotics administered orally. A still further object of this invention is to provide for compositions for the prevention of lactic acidosis in ruminants containing sulfur-containing peptide antibiotics. Further objects will become apparent upon reading the complete disclosure.

It has been discovered that certain antibiotics, specifically that class of antibiotics described as sulfur-containing peptide antibiotics having a molecular weight in excess of 900 which are active against gram positive bacteria, are effective in preventing and treating lactic acidosis in ruminants. Such sulfur-containing peptide antibiotics have been discovered to be narrow spectrum antibiotics particularly effective against *Streptococcus bovis*, however, having no substantial effect at use levels on other rumen microbes, thus allowing for the normal rumen function to continue. The narrow-spectrum, sulfur-containing peptide antibiotics of this invention are defined as those antibiotics which are effective in inhibiting the growth of *Streptococcus bovis* while at the same time having a minimal effect on the growth of the gram negative bacteria normally present in the digestive system of ruminants and which antibiotics are peptidal in nature and contain sulfur as an integral element thereof, and exceed 900 molecular weight.

Examples of such sulfur-containing peptide antibiotics are: thiopeptin, thiostrepton, theiomycetin, amicetin C, siomycin, sporangiomycin, thermothiocin, sulfomycin, multhiomycin, cyromycin, actinotiocin, leucopeptin, arsimycin, sporangiomycin, taitomycin and the like.

In addition to the utility of the above disclosed antibiotics as lactic acidosis preventive agents, they also find utility as growth permittants in ruminants.

The above sulfur-containing peptide antibiotics may be administered orally to a ruminant when the conditions are such that the animal is predisposed to lactic acidosis. That is when it is suspected that ingestion of high carbohyrate feed will cause the fermentation thereof due to the microorganism *Streptococcus bovis* and results in the production of quantities of lactic acid detrimental to the health of the animal. Under such conditions the oral administration of a sulfur-containing peptide antibiotic will result in a prevention of the production of toxic quantities of lactic acid. The antibiotic may be orally administered in a solid dosage from such as a tablet, bolus, capsule and the like or in a liquid unit dosage form such as a drench. In addition the antibiotic may be administered as a component of the animal's normal daily feed ration. That is it may be uniformly admixed with the animal's solid feed or uniformly dispersed or dissolved in the animal's drinking water supply.

When the antibiotics of this invention are included in a drench formulation, it is normally as an aqueous suspension or dispersion of the antibiotic together with a suspending agent such as bentonite and a wetting agent or like excipient. Generally the drenches also contain an antifoaming agent. Preferred drench formulations contain from about 0.1 to 50% by weight of the antibiotic. Especially preferred are drench formulations containing from about 2 to 25% by weight of the antibiotic. When the antibiotics of this invention are employed in a solid unit dosage form such as tablets, capsules and boluses the active ingredient is admixed with a carrier vehicle such as starch, talc, magnesium stearate, or dicalcium phosphate. These dosages forms are prepared by intimately and uniformly mixing the active ingredient with suitable finely divided diluents, fillers disintegrating agents and/or binders such as starch, lactose, talc, magnesium stearate, vegetable gums and the like. The antibiotic may be present in the solid unit dosage formulation at a concentration of from about 0.1 to 95% by weight. Such unit dosage formulations both liquid and solid may be varied widely with respect to their total weight and content of antibiotic agent depending upon factors such as the type of host animal to be treated, and the weight of the host.

When the antibiotic is to be administered via the animal feedstuff it is intimately dispersed in the feed or else used as a top dressing or in the form of pellets which are then added to the finished feed.

The antibiotic agents of this invention find their primary use in the treatment of ruminants such as sheep and cattle. The optimum amount of antibiotic to be employed for the treatment of a particular animal, will depend on the particular antibiotic employed, the species of animal to be treated, and the weight of the animal. Generally good results are obtained with the antibiotics of this invention by the oral administration of from about 0.05 to 10 mg. per kg. of animal body weight per day, such dose being given at one time or in divided doses over a period of time. With the preferred antibiotics of this invention, excellent control of lactic acidosis is obtained in cattle and sheep by administering from about 0.20 to 10 mg. per kg. of body weight in a single dose. The antibiotic may be administered to the ruminant for a period of time which corresponds to the period of time necessary for the animal to become adjusted to the high energy feed that is up to about 30 days. In this way the antibiotic treatment may be withdrawn and the animal allowed to feed normally on the high energy feed. However, as aforementioned an animal already adjusted to high energy feed may sometimes for reasons not fully understood develop lactic acidosis. Thus it may be desirable to maintain the animal on these antibiotics for the entire duration of the animals being fed high energy feed. The techniques for administering these materials to animals are known to those skilled in the veterinary field.

When the antibiotics described herein are administered as a component of the animal's feed or dissolved or suspended in the animal's drinking water, compositions are provided in which the antibiotic is intimately dispersed in an inert carrier or diluent. By inert carrier, is meant one that will not react with the antibiotic and one that may be administered safely to animals. Preferably the carrier is one that is or may be an ingredient of the animal ration.

Suitable compositions include feed supplements in which the active ingredient is present in relatively large amounts and which are suitable for addition into the feed either directly or after an imtermediate dilution or blending step. Such compositions may also be added to the animals feed in the form of a top dressing. Typical carriers or diluents suitable for such compositions include for example distillers dried grains, corn meal, citrus meal, fermentation residues, ground oyster shells, wheat shorts, molasses solubles, corncob meal, edible bean mill feed, soyagrits, crushed limestone and the like. The active antibiotics are intimately dispersed throughout the carrier by methods such as grinding, stirring, milling or tumbling. Compositions containing from about 0.1 to 50% by weight, especially from about 0.5 to 25% by weight of the antibiotic are particularly suitable as feed additives.

Such supplements are added to the animal feed in an amount to give the finished feed the concentration of antibiotic desired for the treatment and control of lactic acidosis. Although the desired concentration of antibiotic will vary depending on the factors previously mentioned as well as upon the particular antibiotic employed, the sulfur-containing peptide antibiotics of this invention are usually fed at concentration of between 0.0002 and 0.02% in the feed in order to achieve the desired effect against lactic acidosis.

The sulfur-containing peptide antibiotics of this invention may be added to the feed supplements and unit dosage forms described above in the form of a purified antibiotic or as a component of the mycelium cake obtained directly from the fermentation broth.

Thiopeptin is a sulfur-containing peptide antibiotic which has proven to be an active agent against lactic acidosis. Thiopeptin has been discovered as being an active agent against *Streptococcus bovis* while, however, being narrow in spectrum and in fact having no effect upon most microorganisms present in ruminants which control the normal digestive function. Furthermore, being of high molecular weight, thiopeptin is retained in the rumen fluid and is not lost by absorption.

For comparison purposes, the activity of a broad spectrum antibiotic was compared with thiopeptin to demonstrate that merely because an antibiotic is active against *Streptococcus bovis* is no indication that said antibiotic will be effective against lactic acidosis.

Thiopeptin is active against *Streptococcus bovis* in an in vitro test at a minimum inhibitory concentration of 0.016 μg per ml. while penicillin G is active at 0.004 μg per ml in the same in vitro test. However, in order to test whether or not antibiotic is effective against lactic acidosis, an in vivo test has been developed in which the efficacy of antibiotics for preventing lactic acidosis can be readily determined.

Lactic acidosis is consistently induced in sheep that have been fasted for 24 hours by dosing then with a slurry of finely ground wheat at 4% of body weight and water (1:2, weight to volume) through a rumen fistula. The pH of rumen fluids samples taken every 2 hours for 28 hours dropped quickly from about 7.0 to 4.0 and remained at about 4.0 until death which occurred between 18 and 40 hours. Lactic acid in the rumen fluid of these sheep increased extremely rapidly from normal levels of about 20 μg. per ml. to over 11,000 μg. per ml. by 8 hours and remain elevated until death. Volatile fatty acids in the rumen fluid increased temporarily but by 12 hours were below the 24 hour starvation levels indicating that almost all normal rumen fermentation was inhibited. Plasma lactic acid levels increased as lactic acidosis developed increasing from a normal range of from about 150 to 400 μg. per ml. to about 1,300 μg. per ml. at death. When penicillin G is administered to the above fistulated sheep at a dose of 150 mg. per sheep at 0 and 6 hours after dosage with ground wheat, there is no observed lactic acidosis, however, almost all rumen fermentation was eliminated. Penicillin G is active against too broad a spectrum of microorganisms, so that it eliminated not only the *Streptococcus bovis* microorganism but also it eliminated most of the other microorganisms in the rumen, thus effectively stopping all digestive processes. Such a situation is not desirable and results in the cessation of the production of volatile fatty acids which are the primary energy source for the animal derived from the digestion of the feed. With the ceased production of volatile fatty acids due to the stoppage of normal rumen function, anorexia, a loss of energy, and either a loss of weight or at least a lack of a gain of weight was observed. Thus penicillin G being too broad a spectrum antibiotic and being active against *Streptococcus bovis* is seen to be unacceptable as an agent for the prevention and cure of lactic acidosis.

Experimental in vivo studies in sheep have shown that thiopeptin at levels of 17.5 mg. per animal or higher successfully prevented lactic acidosis in ruminants. Four groups of 2 fistulated sheep each are dosed with wheat and 17.5, 35, 70 and 140 mg. of thiopeptin (rates of about 0.4, 0.8, 1.75 and 3.5 mg./kg. respectively) in a same manner as previously described for the control of animals. Rumen fluid pH dropped quickly but leveled off at a higher level (4.5 to 5.0) than controls given wheat alone. Rumen fluid lactic acid levels increased moderately after dosing, peaking at about 4,000 μg. per ml. at 8 hours and returning to normal levels of about 20 μg. per ml. by 12 hours after dosing. Plasma lactic acid levels were not altered in thiopeptin protected ruminants. Total volatile fatty acid levels in the rumen fluid of thiopeptin protected ruminants increased over the 30 hours test period from a range of 25 to 50, to 150 to 200 micromoles per ml. indicating that rumen fermentation was not inhibited. Thus thiopeptin at 17.5 mg. or higher per animal (0.4 mg./kg.) protected 8 of 8 ruminants against lactic acidosis following administration of a large quantity of carbohydrate while control animals consistently developed severe lactic acidosis resulting in death.

Studies have been conducted to determine any possible effects of thiopeptin on normal rumen fermentation and/or feed intake of ruminants adapted to various levels of readily fermentable carbohydrate consumption. Two dose levels of thiopeptin (0, 10 and 25 grams per ton) added to 3 rations containing different levels of grain and were fed normally to 9 groups of 2 or 3 sheep each. The animals weighed an average of 45 kg and ate from 1 to 2 kg of feed per day. Ration A contained 32% cracked corn; ration B contained 70% cracked corn; and ration C contained 30% ground corn plus 50% ground wheat. After an adaptation period feed intake is measured daily for 2 weeks and rumen fluid samples taken twice daily on 4 days during a 2 week period and analyzed for volatile fatty acid content. Thiopeptin had no effect on the concentration of acetate, propionate, butyrate or on the concentration of total volatile fatty acids in the rumen fluid. Also thiopeptin did not alter feed intake. These data show that thiopeptin does not have any detrimental effect on rumen fermentation or feed intake.

In addition, thiopeptin has been tested in cattle in an experimental test similar to the above sheep test designed to show its efficacy in preventing lactic acidosis. Fistulated cattle are dosed with a slurry of finely ground wheat at about 4% of body weight and water (1:2 weight to volume) after a starvation period of 48 hours. As in the fistulated sheep test the rumen fluid pH dropped to about 4.0 and blood pH dropped below 7.0 whereupon death occurred in the control animals.

When 0.75 to 1.50 mg./kg. of thiopeptin is administered with the wheat slurry the rumen fluid pH level stabilized at greater than 5 and there was no effect of the blood pH. The control animals invariably died at from 25 to 60 hours while the medicated cattle remained healthy, adjusting to the high energy feed.

Thiostrepton, another sulfur-containing peptide antibiotic has been shown to be equally effective as thiopeptin in inhibiting *Streptococcus bovis* in the in vitro test system. The minimum inhibitory concentration for thiostrepton is 0.016 μg per ml in the in vitro test.

The sulfur containing peptide antibiotics of this invention are best administered to a ruminant at the time when experience has shown it to be highly susceptible to the nutritional disorder lactic acidosis.

Generally when a ruminant animal arrives at a feedlot it has either had no feed at all for the previous 24 hour period or it has had a low energy ration. In either case, it will be necessary to acclimate the animal to the high energy ration of the feedlot. This high energy feedlot ration generally is comprised of 50% or less or roughage feed (such as alfalfa hay, alfalfa silage, corn silage and the like) and 40% or more of cereal or grain (such as corn, milo, wheat or barley). This feed will have an energy content (defined as net energy of the feed for maintenance and production) in excess of about 110 megacalories (Mcal) per kg. of feed. Preferred high energy rations generally contain 50% or more of cereal or grains 30% or less of roughage. Such feed will generally have an energy content of 130 or more megacalories per 100 kg. of feed. The remainder may include such items as fats, molasses and other supplements including vitamin and mineral additives to insure the proper vitamin and mineral balance.

An even more preferred high energy ration will contain 70% or more of cereal or grains and 15% or loss of roughage. This feed will have an energy content of about 155 or more megacalories per 100 kg. of feed. This feed is generally referred to as "finishing feed" since it is the highest energy feed and will afford the most rapid weight gains.

The common practice of acclimating ruminants to a high energy diet by slowly increasing the high energy grain content of a roughage diet over a 3-4 week period is inefficient and uneconomical in that the animals are not gaining weight at the maximum rate and must spend a longer period of time in the feedlot to get to the slaughtering weight. Thus, the instant invention, by preventing lactic acidosis in the ruminant, dramatically shortens the period of time the ruminant requires to become acclimated to a high energy diet. Thus, the total period of time the ruminant spends in the feedlot is shortened as the animal reaches the slaughtering weight in less time than with traditional techniques.

It has been found that lactic acidosis is very likely to occur under three general conditions. The first is when an animal is initially converted to a high energy feed, that is one having an energy content of 110 or more megacalories per 100 kg. and comprising 50% or less roughage and 40% or more of cereal or grain. Before entering the feedlot, generally such animals are on a low energy diet. Most often the animals have been grazed and have received no high energy feed, only roughage. Occasionally the animals may receive supplements containing a low percentage of grain, but this is still not a high energy feed and no lactic acidosis problems are encountered. In practice, when an animal has to be transported from a pasture to a feedlot, it will have received little or no feed during transit, and no high energy feed at all, and the conversiion to a high energy feed will be highly likely to produce lactic acidosis. Thus, the addition of one or more of the above sulfur-containing peptide antibiotics to a feed having an energy content of 110 or more Mcals per 100 kg. when such feed is administered to a ruminant previously having subsisted on a feed containing less than 110 Mcals per 100 kg. will prevent lactic acidosis and shorten the period of adaptation of the ruminant to said high energy feed.

The second condition under which lactic acidosis is likely to occur is when a ruminant is fully adjusted to a high energy feed, such as in a feedlot, and for some reason, stops eating for a period of time. It has been found that when a period of feed deprivation of 6 hours or more occurs and the animal resumes feeding on the high energy feed, lactic acidosis is highly likely to occur. The traditional way this is handled is to resume roughage feeding and then to re-acclimate the animal to a high energy feed over a period of 2-4 weeks. The animal may stop eating for several reasons, there may be natural reasons such as spontaneous inappetence or severe storms; or mechanical reasons such as the breakdown of an automatic feeder or supply truck; or human reasons such as a workman's failure to supply adequate feed to a particular pen. Thus, the addition of a sulfur-containing peptide antibiotic to a feed having an energy content of 110 or more Mcals per 100 kg., and the administration of this medicated feed to an animal which had been deprived of such feed for 6 hours or more, will prevent lactic acidosis and reduce or eliminate the period of time required to re-adapt the animal to a high energy feed. It is noted that since the factors which cause an animal to go "off feed" are highly unpredictable, the continuous administration of such medicated feed to the animals during their entire stay in the feedlot will completely avoid this potential for lactic acidosis.

The third condition under which lactic acidosis may occur is in those animals which have started on a high energy feed with an energy content of at least 110 Mcals per 100 kg. of feed, but have not yet reached the finishing feed at 155 Mcals per 100 kg. or higher. The rapid change from one high energy feed to another high energy feed wherein the latter has an energy content of 10 or more Mcals per 100 kg. over the former may, in some animals, cause lactic acidosis. Lactic acidosis caused under these conditions is not as frequent as in the others, however, occurances in about 10% of a herd are not uncommon. Of course, the greater the difference in energy conent between the first feed and the feed to which the animal is shifted will increase the probability of lactic acidosis and the percentage of animals to come down with the disorder. Thus, where a ruminant is ingesting a feed with an energy content of at least 110 Mcals per 100 kg. and said ruminant is then fed a feed with an energy content of 10 or more Mcals per 100 kg. greater than said first feed, the inclusion of one or more of the above sulfur-containing peptide antibiotic in said second feed will prevent the occurance of lactic acidosis, and shorten or eliminate the period of adaptation of said animal to said higher energy feed.

Lactic acidosis in ruminants can thus now be prevented with this invention by feeding rations containing appropriate levels of thiopeptin or other sulfur-containing peptide antibiotics. This will reduce the incidents of anorexia, rumen disfunction, rumenitis, diarrhea, founder, liver abscesses and death in ruminants, and therefore will improve growth and feed efficiency. This invention will also allow ruminants to be switched rapidly from a low to a high energy ration with none of the above listed effects and thus reduce the time and cost required to fatten ruminants for market.

What is claimed is:

1. A method for the prevention of lactic acidosis in ruminants and for shortening the period of adaptation of said ruminants to a high energy feed from a low energy roughage feed wherein said low energy roughage feed has an energy content of less than 110 megacalories per 100 kg. of feed and said high energy feed has an energy content of 110 or more megacalories per 100 kg. of feed, which comprises administering to said ruminant said high energy feed and an effective amount of a sulfur-containing peptide antibiotic with a molecular weight in excess of 900.

2. The method of claim 1 in which said antibiotic is thiopeptin or thiostrepton.

3. The method of claim 1 in which said antibiotic is administered at a dose of from 0.05 to 10.0 mg. per kg. of animal body weight.

4. The method of claim 3 in which said antibiotic is administered at a dose of from 0.2 to 10.0 mg. per kg. of animal body weight.

5. A method for the prevention of lactic acidosis in ruminants and for shortening the period of adaptation of said ruminants to a high energy feed following a period of starvation which comprises administering to a ruminant which has been deprived of feed for a period in excess of 6 hours, a high energy medicated feed comprising a feed ration having an energy content of 110 or more megacalories per 100 kg. of feed and an effective amount of a sulfur-containing peptide antibiotic with a molecular weight in excess of 900.

6. The method of claim 5 in which said antibiotic is thiopeptin or thiostrepton.

7. The method of claim 5 in which said antibiotic is administered at a dose of from 0.05 to 10.0 mg. per kg. of animal body weight.

8. The method of claim 7 in which said antibiotic is administered at a dose of from 0.2 to 10.0 mg. per kg. of animal body weight.

9. A method for the prevention of lactic acidosis in ruminants and for shortening the period of adaptation of said ruminants to a higher energy feed from a lower energy feed wherein said lower energy feed has an energy content of at least 110 megacalories per 100 kg. of feed and said higher energy feed has an energy content of 10 or more megacalories per 100 kg. higher than said lower energy feed which comprises including in said higher energy feed an effective amount of a sulfur-containing peptide antibiotic having a molecular weight in excess of 900.

10. The method of claim 9 in which said antibiotic is thiopeptin or thiostrepton.

11. The method of claim 9 in which said antibiotic is administered at a dose of from 0.05 to 10.0 mg. per kg. of animal body weight.

12. The method of claim 11 in which said antibiotic is administered at a dose of from 0.2 to 10.0 mg. per kg. of animal body weight.

* * * * *